United States Patent
Omi

(10) Patent No.: US 11,902,695 B2
(45) Date of Patent: Feb. 13, 2024

(54) RADIATION IMAGING SYSTEM, CONTROL APPARATUS, AND CONTROL METHOD

(71) Applicant: CANON KABUSHIKI KAISHA, Tokyo (JP)

(72) Inventor: Hiroyuki Omi, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 188 days.

(21) Appl. No.: 17/381,825

(22) Filed: Jul. 21, 2021

(65) Prior Publication Data

US 2021/0360173 A1   Nov. 18, 2021

Related U.S. Application Data

(63) Continuation of application No. PCT/JP2019/046993, filed on Dec. 2, 2019.

(30) Foreign Application Priority Data

Jan. 24, 2019  (JP) ................. 2019-010540

(51) Int. Cl.
*H04N 5/32*  (2023.01)
*H05G 1/08*  (2006.01)
(Continued)

(52) U.S. Cl.
CPC ............ *H04N 5/32* (2013.01); *H04N 23/80* (2023.01); *H05G 1/085* (2013.01); *H05G 1/42* (2013.01)

(58) Field of Classification Search
CPC ......... A61B 6/032; A61B 6/542; A61B 6/545; A61B 6/488; A61B 6/585; A61B 6/4233;
(Continued)

(56) References Cited

U.S. PATENT DOCUMENTS 10,016,176 B2   7/2018  Omi
10,825,189 B2   11/2020  Omi
(Continued)

FOREIGN PATENT DOCUMENTS

JP   2002177264 A   6/2002
JP   2009-273594 A  11/2009
(Continued)

OTHER PUBLICATIONS

International Search Report issued by the Japan Patent Office dated Mar. 3, 2020 in corresponding International Application No. PCT/JP2019/046993, with English translation.
(Continued)

*Primary Examiner* — Irakli Kiknadze
(74) *Attorney, Agent, or Firm* — Carter, DeLuca & Farrell LLP

(57) ABSTRACT

A control apparatus that controls, using automatic exposure control of controlling a radiation generation apparatus by comparing a radiation dose from the radiation generation apparatus with a target dose, radiation imaging using radiation from the radiation generation apparatus, comprises a processing unit that executes image processing on a radiation image obtained by the radiation imaging; and a setting unit that sets, as the target dose used in the automatic exposure control, a dose which is changed in accordance with an image processing parameter for executing the image processing.

17 Claims, 5 Drawing Sheets

(51) Int. Cl.
*H05G 1/42* (2006.01)
*H04N 23/80* (2023.01)

(58) Field of Classification Search
CPC ......... A61B 6/00; A61B 6/4435; A61B 6/544;
A61B 6/5294; A61B 6/46; A61B 6/54;
A61B 6/44; A61B 6/4429; A61B 6/40;
A61B 6/035; A61B 6/5258; A61B 6/467;
A61B 6/465; A61B 6/5205; A61B
6/4291; A61B 8/0825; A61B 5/055; A61B
6/5211; A61B 6/4417; A61B 8/483; A61B
6/461; A61B 8/14; A61B 6/025; A61B
6/5217; A61B 6/502; A61B 34/30; A61B
6/037; A61B 6/4411; A61B 5/117; A61B
6/547; A61B 6/469; A61B 5/0037; A61B
6/50; A61B 5/1128; A61B 5/1176; A61B
5/704; A61B 5/1079; A61B 6/484; A61B
6/4035; A61B 6/4447; A61B 6/4488;
A61B 6/06; G06N 20/00; G06N 3/08;
G06T 7/0012; G06T 2207/20081; G06T
2207/10144; G06T 2207/30168; G06T
2207/10081; G06T 2207/30004; G06T
7/0014; G06T 2207/10128; G06V 10/25;
H05G 1/30; H05G 1/42; H05G 1/44;
H05G 1/085; H05G 1/26; H05G 1/32;
H05G 1/34; H05G 1/265; H05G 1/46;
H05G 1/08; H05G 1/56; H05G 1/36;
G01T 1/02; H04N 23/80; H04N 5/32;
G16H 50/20; G16H 50/50; G16H 30/40;
G16H 40/63; G16H 40/67; G16H 20/40;
G16H 50/70; G16H 30/20; G01N 23/041;
G21K 1/10; G21K 1/04; H01J 35/26;
H01J 2235/085
USPC .......................................................... 378/62
See application file for complete search history.

(56) References Cited

U.S. PATENT DOCUMENTS

| | | | |
|---|---|---|---|
| 11,000,253 | B2 | 5/2021 | Omi |
| 2009/0285464 | A1* | 11/2009 | Urushiya .................. G06T 5/50 |
| | | | 382/131 |
| 2016/0183908 | A1* | 6/2016 | Hayashida ........... A61B 6/4291 |
| | | | 378/207 |
| 2016/0377737 | A1* | 12/2016 | Okada ...................... H04N 5/32 |
| | | | 250/394 |
| 2017/0202534 | A1* | 7/2017 | Crotty .................... A61B 6/465 |
| 2018/0055473 | A1* | 3/2018 | Torii ....................... A61B 6/542 |
| 2019/0099148 | A1* | 4/2019 | Rupcich ................... H05G 1/26 |

FOREIGN PATENT DOCUMENTS

| | | |
|---|---|---|
| JP | 2014-012109 A | 1/2014 |
| JP | 2014-151036 A | 8/2014 |
| JP | 2015-092913 A | 5/2015 |
| JP | 2016-198469 A | 12/2016 |
| JP | 2017-126860 A | 7/2017 |
| JP | 2018-192129 A | 12/2018 |
| JP | 2018201685 A | 12/2018 |

OTHER PUBLICATIONS

Funahashi, M., The Evolution of DR Systems 2017, Still Image Edition: Evolution of FPD and New Dimensions in Digital Radiography, 4. Outline of technique for removing scattered radiation, "3. Clinical application", INNERVISION (Oct. 23, 2017) vol. 32, No. 11, pp. 19-23, together with English explanation.

Matsuo, K., "Improvement in Medical Service Resulting from Usage of FUJIFILM DR CALNEO AQRO: From the viewpoint of low dosage but high quality, and reduction in operating costs" Shin Iryou, October Edition (Oct. 1, 2018) pp. 127-140, together with English explanation.

Notice of Reasons for Refusal issued by the Japan Patent Office dated Sep. 2, 2022 in corresponding JP Patent Application No. 2019-010540, with English translation.

* cited by examiner

| SCATTERED RAY REDUCTION PROCESSING | TARGET DOSE |
|---|---|
| ON | a |
| OFF | b |

5b

| SCATTERED RAY REDUCTION PROCESSING | GRID SPECIFICATION | TARGET DOSE |
|---|---|---|
| ON | – | a |
| OFF | A | b1 |
| | B | b2 |

5c

| SCATTERED RAY REDUCTION PROCESSING | NOISE REDUCTION PROCESSING | TARGET DOSE |
|---|---|---|
| ON | OFF | a |
| | X | a11 |
| | Y | a12 |
| OFF | OFF | b |
| | X | b11 |
| | Y | b12 |

5d

| SCATTERED RAY REDUCTION PROCESSING | REDUCTION EFFECT | TARGET DOSE |
|---|---|---|
| ON | 1 | a21 |
| | 2 | a22 |
| | 3 | a23 |
| OFF | – | b |

RADIATION IMAGING SYSTEM, CONTROL APPARATUS, AND CONTROL METHOD

CROSS-REFERENCE TO RELATED APPLICATIONS

This application is a Continuation of International Patent Application No. PCT/JP2019/046993, filed Dec. 2, 2019, which claims the benefit of Japanese Patent Application No. 2019-010540, filed Jan. 24, 2019, both of which are hereby incorporated by reference herein in their entirety.

BACKGROUND OF THE INVENTION

Field of the Invention

The present invention relates to a radiation imaging system, a control apparatus for automatic exposure control in radiation imaging, and a control method.

Background Art

In the medical site, in order to obtain a radiation image having appropriate image quality while suppressing the exposure dose to the patient, automatic exposure control (to be referred to as AEC hereinafter) is executed. AEC is a mechanism of detecting the radiation dose by a dose detection sensor during irradiation of radiation, and stopping the irradiation of radiation by a radiation source when the integrated value (accumulated dose) of the detected doses reaches a preset target dose (PTL 1). When the irradiation of radiation is stopped, a radiation imaging apparatus shifts the operation of a flat panel detector (to be referred to as an FPD hereinafter) from an accumulation operation to a readout operation, and obtains a radiation image.

In radiation imaging, two components including primary radiation rectilinearly transmitted through the object and scattered rays scattered by the object are generated. Since the scattered rays are superimposed on the image as extremely low frequency components in the structure of the object, the contrast of the entire image is decreased, which causes a decrease in diagnostic performance. In order to prevent such a deterioration in image quality of a radiation image, a slit-shaped grid called a grid is provided between the object and the FPD. This reduces the scattered rays entering the FPD by blocking, in front of the FPD, the scattered rays not traveling rectilinearly. On the other hand, a technique has also been proposed, which reduces, by image processing (scattered ray reduction processing), the scattered ray components in a radiation image captured without using the grid (PTL 2). In order to obtain equal image qualities in a case of using the scattered ray reduction processing without using the grid and a case of using the grid without using the scattered ray reduction processing, equal irradiation doses are required.

CITATION LIST

Patent Literature

PTL 1: Japanese Patent Laid-Open No. 2017-126860
PTL 2: Japanese Patent Laid-Open No. 2016-198469

If a grid for scattered ray reduction is used, the radiation attenuated by the grid reaches the AEC dose detection sensor. On the other hand, in the configuration in which the scattered ray components of a radiation image obtained by executing imaging without using the grid is reduced by scattered ray reduction processing, the radiation reaches the dose detector sensor without being attenuated by the grid. Therefore, when the target dose in AEC is the same, if AEC is operated without using the grid, the accumulated dose reaches the target dose with less irradiation doses than in a case of using the grid, and the irradiation of radiation is stopped. That is, in the configuration using the scattered ray reduction processing (configuration using no grid), if a radiation image is captured using a target dose assuming use of the grid, the radiation dose is insufficient and it is difficult to obtain a radiation image having appropriate image quality.

In one aspect of the present invention, a technique is provided which controls setting of a target dose in automatic exposure control so that radiation imaging can be executed with an appropriate radiation dose.

SUMMARY OF THE INVENTION

According to one aspect of the present invention, there is provided a control apparatus that controls, using automatic exposure control of controlling a radiation generation apparatus by comparing a radiation dose from the radiation generation apparatus with a target dose, radiation imaging using radiation from the radiation generation apparatus, comprising: a processing unit configured to execute image processing on a radiation image obtained by the radiation imaging; and a setting unit configured to set, as the target dose used in the automatic exposure control, a dose which is changed in accordance with an image processing parameter for executing the image processing.

According to another aspect of the present invention, there is provided a control method for controlling, using automatic exposure control of controlling a radiation generation apparatus by comparing a radiation dose from the radiation generation apparatus with a target dose, radiation imaging using radiation from the radiation generation apparatus, the method comprising: executing image processing on a radiation image obtained by the radiation imaging; and setting, as the target dose used in the automatic exposure control, a dose which is changed in accordance with an image processing parameter for executing the image processing.

According to another aspect of the present invention, there is provided a radiation imaging system comprising: a radiation generation unit configured to emit radiation; an image generation unit configured to generate a radiation image by receiving the radiation from the radiation generation unit; a detection unit configured to detect a radiation dose from the radiation generation unit; a control unit configured to control the radiation generation unit by comparing the radiation dose detected by the detection unit with a target dose; an image processing unit configured to process the radiation image generated by the image generation unit; and a setting unit configured to set, as the target dose used by the control unit, a dose which is changed in accordance with an image processing parameter for executing image processing.

According to another aspect of the present invention, there is provided a non-transitory computer-readable storage medium storing a program for causing a computer to execute a control method for controlling, using automatic exposure control of controlling a radiation generation apparatus by comparing a radiation dose from the radiation generation apparatus with a target dose, radiation imaging using radiation from the radiation generation apparatus, the method comprising: executing image processing on a radiation image obtained by the radiation imaging; and setting, as the target dose used in the automatic exposure control, a dose which is changed in accordance with an image processing parameter for executing the image processing.

Further features of the present invention will become apparent from the following description of exemplary embodiments with reference to the attached drawings.

BRIEF DESCRIPTION OF THE DRAWINGS

FIG. 5 is a view showing examples of tables each for selecting a target dose.

DESCRIPTION OF THE EMBODIMENTS

Figure 1:
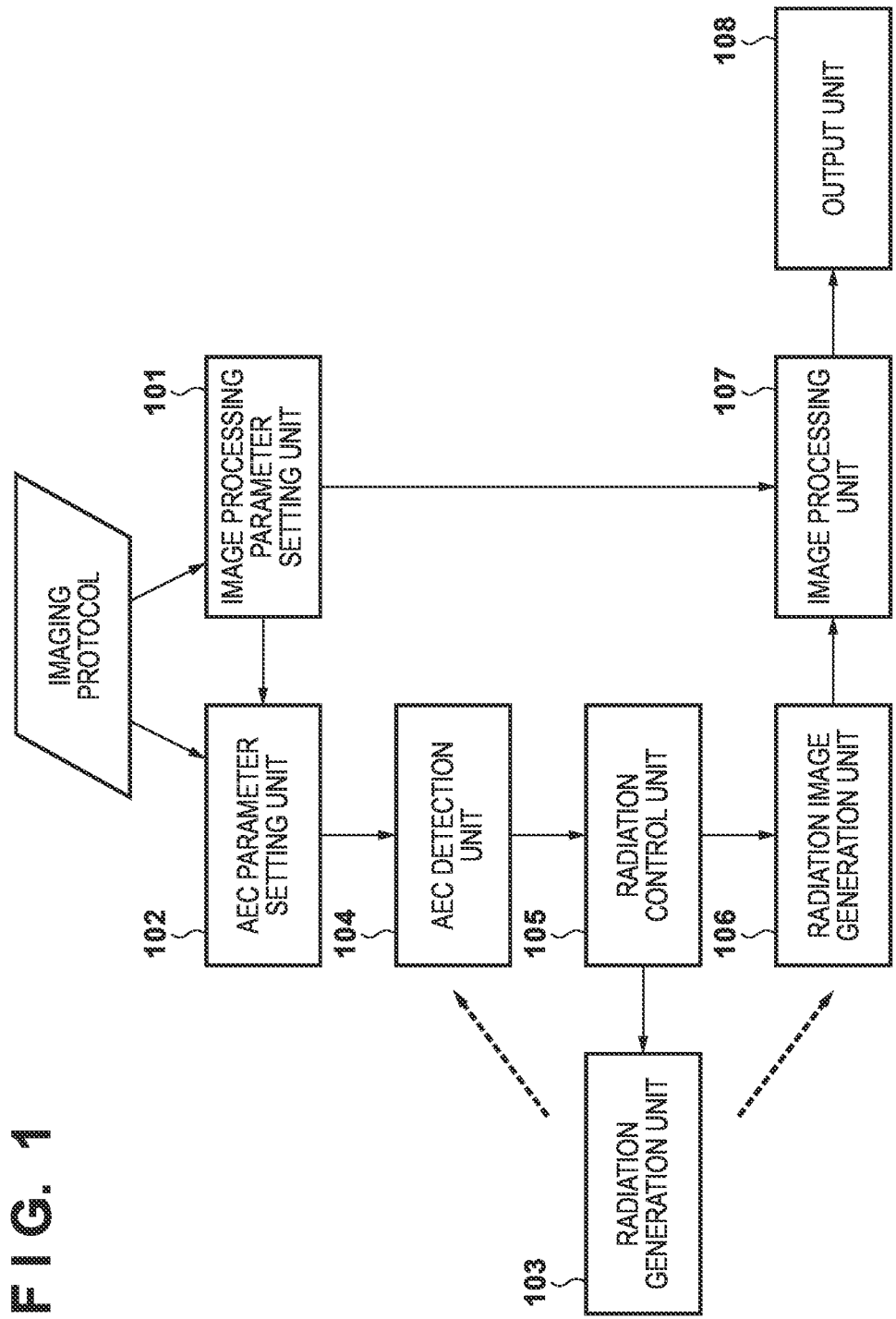
FIG. 1 is a block diagram showing a functional arrangement example of a radiation imaging apparatus according to an embodiment.

Hereinafter, embodiments will be described in detail with reference to the attached drawings. Note, the following embodiments are not intended to limit the scope of the claimed invention. Multiple features are described in the embodiments, but limitation is not made an invention that requires all such features, and multiple such features may be combined as appropriate. Furthermore, in the attached drawings, the same reference numerals are given to the same or similar configurations, and redundant description thereof is omitted.

A radiation imaging system described in each of following embodiments may be a single apparatus including a radiation generation apparatus that emits radiation and a radiation sensor that forms a radiation image, or at least part of the system may exist as a discrete and independent apparatus. In addition, radiation may be X-rays or another type of radiation. In the following embodiments, the term "radiation" can include, for example, a-rays, p-rays, y-rays, particle rays, and cosmic rays in addition to X-rays.

First Embodiment

FIG. 1 is a block diagram showing a functional arrangement example of a radiation imaging system according to the first embodiment. The radiation imaging system includes an image processing parameter setting unit 101, an AEC parameter setting unit 102, a radiation generation unit 103, an AEC detection unit 104, a radiation control unit 105, a radiation image generation unit 106, an image processing unit 107, and an output unit 108.

The image processing parameter setting unit 101 receives a set imaging protocol, and outputs an image processing parameter corresponding to the imaging protocol. The AEC parameter setting unit 102 receives the set imaging protocol and the image processing parameter, and outputs a target dose to be used in automatic exposure control (to be also referred to as AEC). Note that the target dose is determined based on the conditions of the object such as the imaging part, sex, and age from the viewpoint of a diagnostic purpose and an exposure dose. For example, when imaging the body trunk or the like, it is necessary to emit a lot of radiation since X-rays do not easily pass through the body trunk. Therefore, in that case, a high target dose is set to increase the dose reaching the FPD. However, even in a case of imaging the body trunk, if the diagnosis allows for noisy image quality, a low target dose is set to decrease the irradiation dose to the object. In this example, the target dose assumes use of a predetermined grid, and prepared in advance in correspondence with the imaging protocol.

The radiation generation unit 103 generates radiation in accordance with an input of an irradiation signal from the radiation control unit 105. The AEC detection unit 104 receives the radiation transmitted through the object and the target dose, and outputs a radiation control signal. The radiation control unit 105 receives the radiation control signal, and outputs an irradiation stop signal and an image readout signal. The radiation generation unit 103 stops generation of radiation in accordance with the irradiation stop signal from the radiation control unit 105.

The radiation image generation unit 106 generates a radiation image corresponding to the radiation transmitted through the object, and outputs the generated radiation image in accordance with the image readout signal from the radiation control unit 105. The image processing unit 107 is an example of a processing unit that executes image processing on a radiation image obtained by radiation imaging. The image processing unit 107 in this embodiment receives the radiation image and the image processing parameter, and outputs the radiation image having undergone the image processing. For example, the image processing unit 107 executes scattered ray reduction processing on the radiation image in accordance with the image processing parameter. The output unit 108 outputs, to a monitor, a hard disk, a PACS, or the like, the radiation image having undergone the image processing output from the image processing unit 107.

Figure 2:
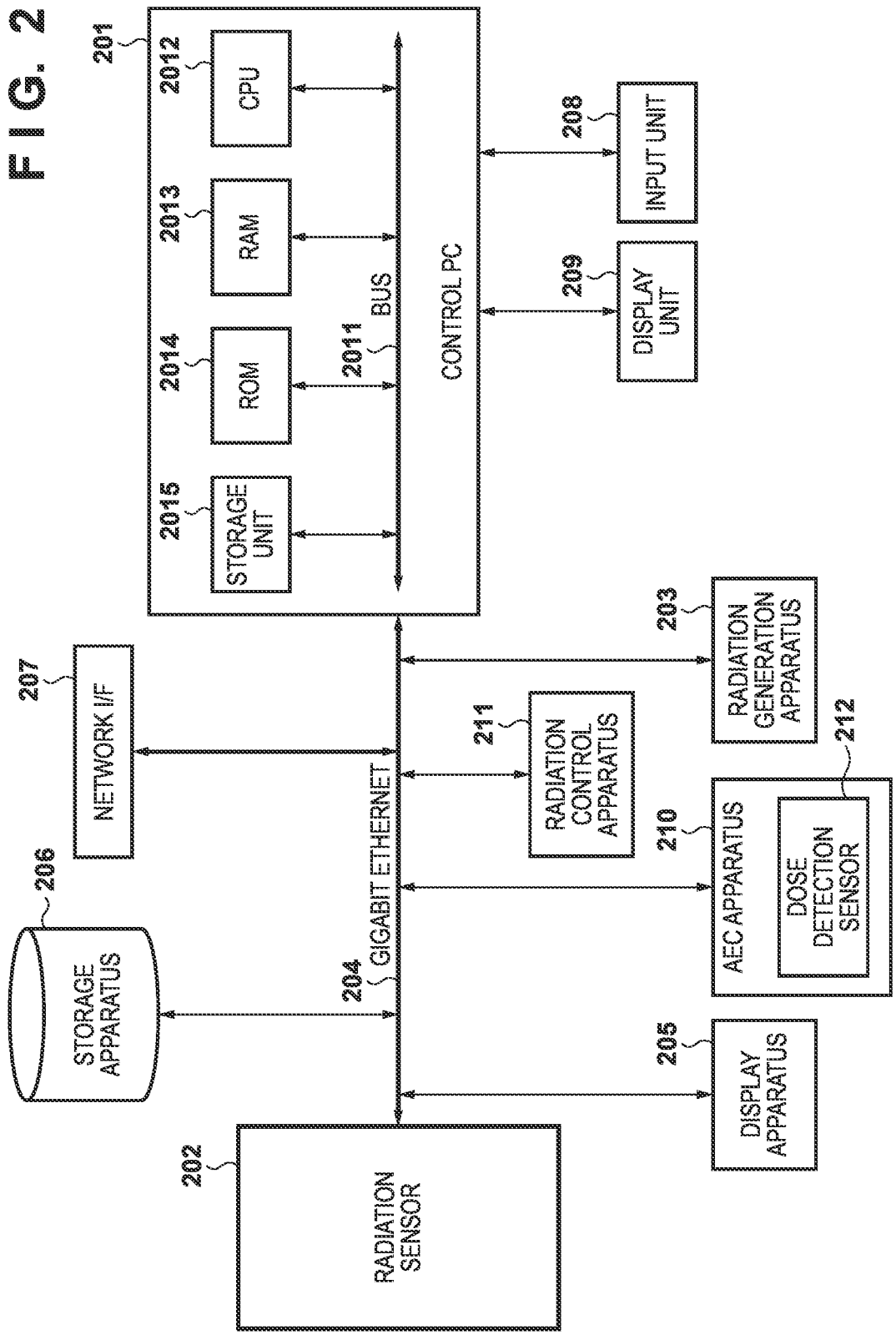
FIG. 2 is a block diagram showing a hardware arrangement example of the radiation imaging apparatus according to the embodiment.

An example of the hardware arrangement for implementing the functional arrangement shown in FIG. 1 will be described with reference to FIG. 2. FIG. 2 is a block diagram showing a hardware arrangement example of the radiation imaging system according to the first embodiment. In this embodiment, the arrangement is shown in which an imaging control apparatus that controls radiation imaging is implemented using a personal computer (to be referred to as a control PC 201 hereinafter).

The control PC 201 and a radiation sensor 202 are connected by a GigaBit Ethernet 204. In a case of long-length imaging using a plurality of radiation sensors, the plurality of radiation sensors are connected to the GigaBit Ethernet 204 as a signal line. Note that the signal line is not limited to the GigaBit Ethernet but may be, for example, a CAN (Controller Area Network), an optical fiber, or the like. In addition to the control PC 201 and the radiation sensor 202, a radiation generation apparatus 203, a display apparatus 205, a storage apparatus 206, network interface 207, an AEC apparatus 210, a radiation control apparatus 211, and the like are connected to the GigaBit Ethernet 204.

In the control PC 201, a CPU (Central Processing Unit) 2012, a RAM (Random Access Memory) 2013, a ROM (Read Only Memory) 2014, and a storage unit 2015 are connected to a bus 2011. The control PC 201 and an input unit 208 are connected via a USB, PS/2, or the like, and the control PC 201 and a display unit 209 are connected via VGA, DVI, or the like. The control PC 201 can transmit commands to the radiation sensor 202, the display apparatus 205, the radiation control apparatus 211, and the like via the GigaBit Ethernet 204. In the control PC 201, various kinds of processing contents are stored as software modules in the storage unit 2015. The CPU 2012 deploys a necessary software module from the storage unit 2015 in the RAM 2013 to execute it.

The function of the radiation generation unit 103 shown in FIG. 1 is implemented by the radiation generation apparatus 203, the function of the radiation image generation unit 106 is implemented by the radiation sensor 202, and the function of the radiation control unit 105 is implemented by the radiation control apparatus 211. The function of the AEC detection unit 104 is implemented by the AEC apparatus 210. The AEC apparatus 210 includes a dose detection sensor 212 that detects the irradiated radiation dose, and executes automatic exposure control based on comparison between the radiation dose detected by the dose detection sensor 212 and the target dose. The dose detection sensor 212 may be implemented by an ion chamber, or may be implemented by a dose detection sensor (see PTL 1) incorporated in the radiation sensor 202.

The control PC 201 is an example of a control apparatus that controls, by using automatic exposure control for controlling a radiation generation apparatus based on comparison between the radiation dose from the radiation generation apparatus and the target dose, radiation imaging using radiation from a radiation generation apparatus. The respective functions of the image processing parameter setting unit 101, the AEC parameter setting unit 102, the image processing unit 107, and the output unit 108 are implemented by the control PC 201. These functions can be implemented by the CPU 2012 executing the software modules stored in the storage unit 2015, but some or all of these functions may be implemented by dedicated hardware.

Note that in the above description, the arrangement in which the control PC 201 implements the image processing unit 107 has been exemplified, but the present invention is not limited to this. The image processing unit 107 may be implemented as a dedicated image processing board. As the destination of the radiation image output from the output unit 108 shown in FIG. 1, for example, the display apparatus 205, the storage apparatus 206, or the PACS connected via the GigaBit Ethernet 204, or the display unit 209 connected to the control PC 201 is used. PACS is the abbreviation of Picture Archiving and Communication Systems.

Figure 3:
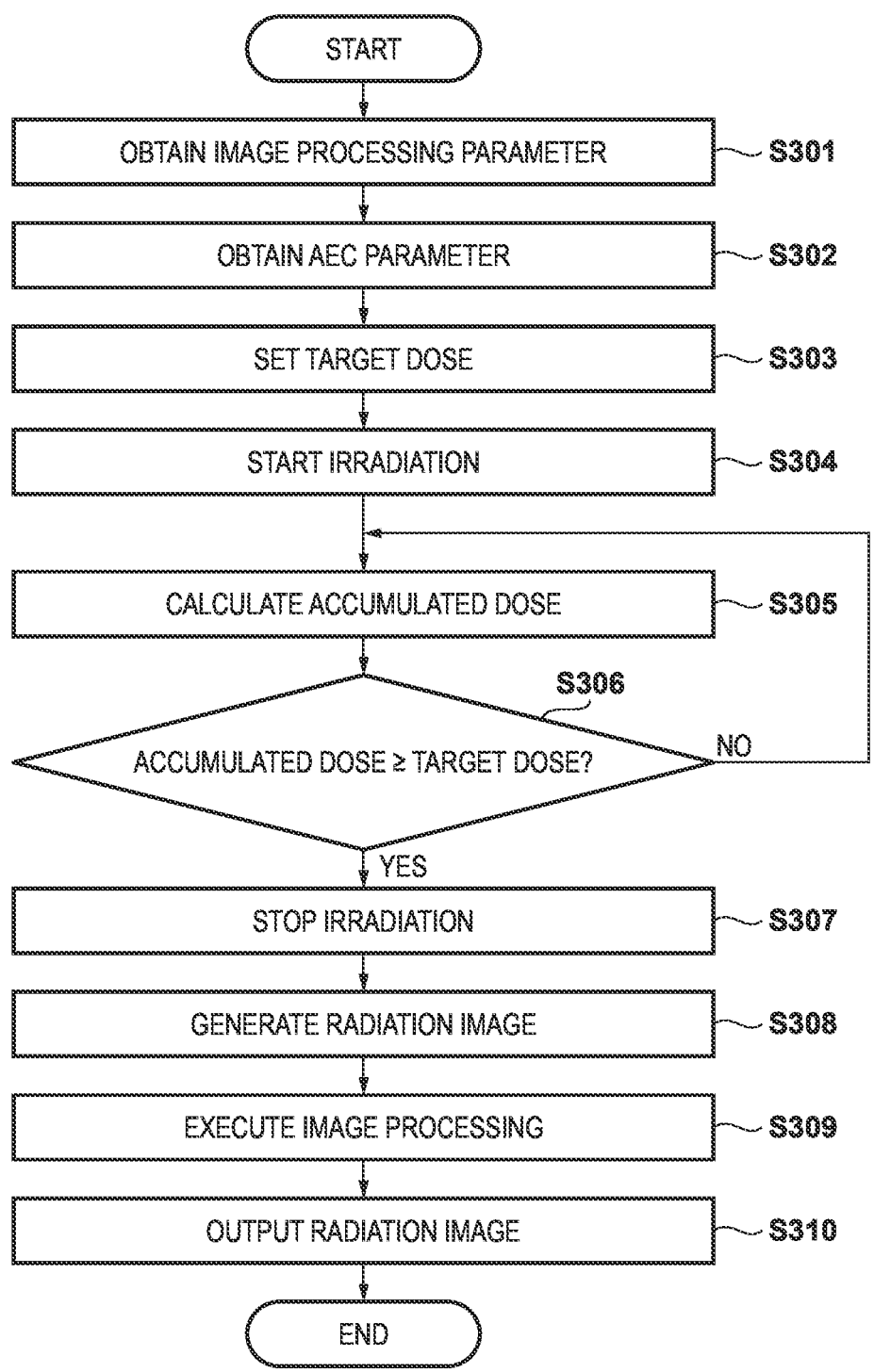
FIG. 3 is a flowchart illustrating a radiation image imaging operation executed by a radiation imaging system.

Next, a radiation imaging operation using automatic exposure control executed by the radiation imaging system according to the first embodiment having the arrangement as described above will be described with reference to a flowchart of FIG. 3.

The image processing parameter setting unit 101 obtains an image processing parameter from an imaging protocol set by a user (step S301). A plurality of imaging protocols are prepared, and the user selects and sets the imaging protocol using, for example, the input unit 208 in accordance with the imaging part or the imaging method. The imaging part and the imaging method can be obtained from, for example, RIS (Radiology Information Systems) or the like. The imaging protocol may be automatically obtained from the RIS or the like. The imaging protocol is a package of various kinds of parameters necessary for imaging, and the parameter (image processing parameter) required upon executing image processing is also included therein. The image processing parameter includes, for example, a parameter indicating ON/OFF of each processing such as scattered ray reduction processing or noise reduction processing, or a detailed parameter regarding the reduction effect of the scattered ray reduction processing, the kernel, or the like.

Then, in steps S302 and S303, the AEC parameter setting unit 102 sets an appropriate target dose in the AEC apparatus 210 in accordance with the image processing to be executed. The AEC parameter setting unit 102 that executes steps S302 and S303 is an example of a setting unit that sets the dose, which changes in accordance with the image processing parameter for executing the image processing, as the target dose used in automatic exposure control. First, the AEC parameter setting unit 102 obtains a parameter (to be referred to as an AEC parameter hereinafter) related to AEC from the set imaging protocol (step S302). The AEC parameter includes, for example, the specification (for example, the grid ratio, the number of grids, and the like) of the grid to be used, and the target dose in AEC using this grid. As has been described above, the target dose is used by the AEC apparatus 210 to instruct a stop of irradiation of radiation.

Then, the AEC parameter setting unit 102 sets a target value in AEC (step S303). At this time, the AEC parameter setting unit 102 corrects the target dose obtained in step S302 based on the image processing parameter obtained in step S301 and the AEC parameter, as needed (step S303). The target dose obtained in step S302 is a value set assuming the radiation imaging using the grid. For imaging with the obtained imaging parameter indicating ON of the scattered ray reduction processing without using the grid, if the target dose obtained in step S302 is used intact, correct dose control is not executed as described below.

Figure 4:
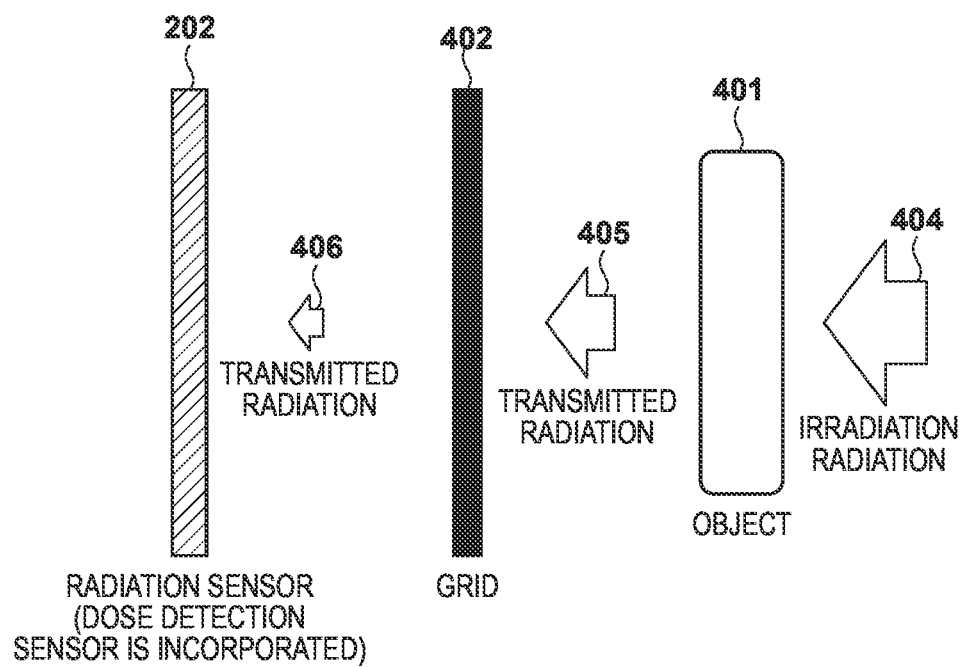
FIG. 4 is a view for explaining the dose of transmitted radiation.

FIG. 4 is a view showing changes in dose of transmitted radiation caused by intervention of a grid. As shown in FIG. 4, irradiation radiation 404 emitted to an object 401 is attenuated mainly by the object 401, and becomes transmitted radiation 405. In a case in which a grid 402 is used, the transmitted radiation 405 is further attenuated by the grid 402, becomes transmitted radiation 406, and reaches the radiation sensor 202. On the other hand, in a case in which the scattered ray reduction processing is ON and the grid 402 is not used, the transmitted radiation 405 is not attenuated by the grid 402 and reaches the radiation sensor 202. Therefore, the dose per unit time reaching the radiation sensor 202 is higher in the case in which the scattered ray reduction processing is ON (the grid is not used) than in the case in which the scattered ray reduction processing is OFF (the grid is used). As a result, if the target dose in AEC is the same, the time from the start to the end of the irradiation of radiation is shorter in the case in which the scattered ray reduction processing is ON than in the case in which the scattered ray reduction processing is OFF, and the radiation irradiation amount (dose) is insufficient in the radiation imaging in the case in which the scattered ray reduction processing is ON.

The attenuated amount of the radiation by the grid 402 depends on the grid ratio, the number of grids, and the material of the grid 402. For example, an aluminum grid whose grid ratio is 10:1 and includes 40 grids attenuates the radiation by about half. In this case, if imaging is executed with the scattered ray reduction processing set ON without using the grid 402, the imaging is executed with the dose half of that in the case in which the scattered ray reduction processing is OFF (the grid is used), and this causes a deterioration in image quality of the radiation image.

In order to prevent the insufficient dose as described above, the AEC parameter setting unit 102 corrects the target dose in AEC obtained in step S302 based on the image processing parameter/AEC parameter (step S303). If the scattered ray reduction processing is to be executed, the AEC parameter setting unit 102 according to the first embodiment corrects, based on the transmission rate of the grid, the target dose assuming use of the grid. More specifically, the AEC parameter setting unit 102 obtains, from the AEC parameter, the grid information (the grid ratio, the number of grids, the material, and the like) of the grid which the target dose assumes, and reflects, on the target dose, the amount which is no longer attenuated by the grid. More specifically, a radiation transmission rate T0 of the grid obtained from the grid information is calculated, and a target dose Th0 is corrected as expressed by following equation (1) to obtain a corrected target dose Th1:

$$Th1 = Th0/T0 \qquad (1)$$

By executing AEC using the corrected target dose Th1, even in the case in which the scattered ray reduction processing is ON (the grid is not used), irradiation of the radiation of the dose equal to that in the case in which the scattered ray reduction processing is OFF (the grid is used) is achieved. As a result, it is possible to prevent a deterioration in image quality due to the insufficient dose. In the case in which the scattered ray reduction processing is ON, the AEC parameter setting unit 102 replaces the target dose obtained in step S302 with the corrected target dose in step S303, and sets it as the AEC-related parameter in the AEC detection unit 104. In this manner, in the case in which the image processing parameter indicates execution of the scattered ray reduction processing, the AEC parameter setting unit 102 sets a first target dose (corrected target dose Th1) in the AEC detection unit 104. In the case in which the image processing parameter indicates non-execution of the scattered ray reduction processing, the AEC parameter setting unit 102 sets a second target dose (uncorrected target dose Th0) different from the first target dose in the AEC detection unit 104. Here, as is apparent from equation (1), the first target dose (Th1) is higher than the second target dose (Th0). Further, the radio of the first target dose and the second target dose is equal to the transmission rate (T0) of the grid assumed by the second target amount.

Then, when a press of an irradiation switch by the user is detected, the radiation control unit 105 outputs an irradiation signal to the radiation generation unit 103. When the irradiation signal is received, the radiation generation unit 103 starts irradiation of radiation (step S304). Note that the irradiation switch may be directly connected to the radiation generation apparatus 203. The AEC detection unit 104 accumulates the doses of radiations reaching it to calculate an accumulated dose (step S305). Further, the AEC detection unit 104 compares the accumulated dose calculated in step S305 with the target dose set in step S303 (step S306). If the accumulated dose has not reached the target dose (NO in step S306), the AEC detection unit 104 continues calculation of the accumulated dose (step S305). In this case, in order to cause the radiation generation unit 103 to continue the irradiation of radiation, the AEC detection unit 104 outputs a continuation request signal as a control request signal to the radiation control unit 105.

If it is determined that the accumulated dose has reached the target dose (YES in step S306), the AEC detection unit 104 outputs a stop request signal as the control request signal (step S307). If the stop request signal is received from the AEC detection unit 104, the radiation control unit 105 transmits an irradiation stop signal to the radiation generation unit 103 to stop the irradiation of radiation. Further, the radiation control unit 105 transmits an image readout signal to the radiation image generation unit 106. Note that if the continuation request signal is transmitted as the control request signal from the AEC detection unit 104, the radiation control unit 105 executes no operation in particular.

Note that the calculation of the accumulated dose in step S305 is repeated at preset time intervals (predetermined cycle). The repeat end condition is that the accumulated dose becomes equal to or higher than the corrected target dose. However, if a metal with a high radiation absorption rate is included in the region where the accumulated dose is calculated, the accumulated dose does not easily reach the corrected target dose. As a result, irradiation of an excessive dose occurs. To prevent this, a timeout may be added to the repeat end condition.

If the image readout signal is received from the radiation control unit 105, the radiation image generation unit 106 reads out an image from the radiation sensor 202 and generates a radiation image (step S308). The image processing unit 107 executes image processing on the generated radiation image based on the set image processing parameter (step S309). Thus, the captured radiation image undergoes the image processing and becomes the image acceptable for a doctor's diagnosis. As the image processing, processing of correcting the basic characteristics of the FPD and processing of emphasizing the structure of the object so as to improve the diagnostic performance of the doctor are executed. The image processing can be classified into pre-processing and post-processing. The pre-processing is processing of correcting the characteristics of the FPD, and offset correction (dark current correction), gain correction, defect correction, and the like are executed. Owing to the pre-processing, the radiation image is set in a state in which the correlation with peripheral pixels is maintained. The post-processing is processing of generating an image suitable for diagnosis, and includes frequency processing, tone processing, and the like are executed. The scattered ray reduction processing is also included in the post-processing.

Finally, the output unit 108 outputs the radiation image having undergone the image processing by the image processing unit 107 (step S310). Thus, the radiation image is provided to the doctor. Examples of the output destination of the output unit 108 are, in addition to the display apparatus 205 and the display unit 209, the PACS via the network interface 207.

As has been described above, according to the first embodiment, it is determined, based on the image processing parameter, whether to execute the scattered ray reduction processing. If it is determined that the scattered ray reduction processing is executed, the target dose in AEC is corrected so that the radiation imaging is executed with the radiation dose equal to that in a case of using the grid. Therefore, even in a case in which the scattered rays are reduced by the image processing (scattered ray reduction processing) without using the grid, the radiation image with the dose maintained can be obtained.

Second Embodiment

In the first embodiment, an example has been described in which the AEC parameter setting unit 102 corrects the target dose in AEC using the specification (the grid ratio, the number of grids, and the like) of the grid defined by the AEC parameter of the imaging protocol. In the second embodiment, a plurality of target doses corresponding to the image processing parameters are prepared, and an AEC parameter setting unit 102 sets, as the target dose in automatic exposure control, the target dose selected from the plurality of target doses in accordance with the image processing parameter. For example, the AEC parameter setting unit 102 sets the target dose using a table in which a combination of the image processing parameter and the AEC-related parameter and the target dose are associated with each other and registered. Note that the functional arrangement and hardware arrangement of a radiation imaging system according to the second embodiment are similar to those in the first embodiment (FIGS. 1 and 2). An operation of the radiation imaging system according to the second embodiment will be described below using the flowchart of FIG. 3.

The AEC parameter setting unit 102 selects, from a plurality of target doses including a target dose for a case of executing scattered ray reduction processing and a target dose for a case of executing no scattered ray reduction processing, the target dose to be used in automatic exposure control, and sets it as the target dose in AEC (step S303). As apart of the AEC-related parameter, a control PC 201 prepares in advance, as a table, a target dose for a case in which the scattered ray reduction processing is ON and a target dose for a case in which the scattered ray reduction processing is OFF. Reference numeral 5*a* in FIG. 5 indicates an example of such a table. According to the table 5*a*, a target dose "a" is selected if the scattered ray reduction processing is ON, and a target dose "b" is selected if the scattered ray reduction is OFF. The AEC parameter setting unit 102 obtains the target dose from the table 5*a* based on the image processing parameter (based on whether the scattered ray reduction processing is ON or OFF), and sets it in an AEC apparatus 210.

As has been described above, according to the second embodiment, if the scattered ray reduction processing is ON, the target dose for the case in which the scattered ray reduction processing is ON (for the case in which no grid is used) is selected. On the other hand, if the scattered ray reduction processing is OFF, the target dose for the case in which the scattered ray reduction processing is OFF (for the case in which a grid is used) is selected.

Note that in the above description, the configuration has been described in which two kinds of target doses respectively corresponding to ON/OFF of the scattered ray reduction processing are prepared, and one of these target doses is selected. However, the present invention is not limited to this. For example, target doses corresponding to the grid specifications may be prepared as a plurality of selectable target doses and, if no scattered ray reduction processing is to be executed, the AEC parameter setting unit 102 may select the target dose corresponding to the grid specification indicated by the grid information. For example, as shown in a table 5*b* in FIG. 5, a plurality of target doses (b1 and b2) corresponding to the specifications (the grid ratio and the number of grids) of the grid may be prepared and, if the scattered ray reduction processing is OFF, one of the target doses b1 and b2 may be selectable based on the specification of the attached grid. Note that the grid information is included in, for example, an AEC parameter.

Further, the target dose may be prepared and selectable for each of not only ON/OFF of the scattered ray reduction processing but also ON/OFF of various image processing or detailed parameters. For example, as shown in a table 5*c* in FIG. 5, for each ON/OFF of the scattered ray reduction processing, a target dose corresponding to noise reduction processing may be prepared. In the table 5*c*, the target dose is prepared for each of a case in which the noise reduction processing is "OFF", a case in which the reduction effect of the noise reduction processing to be executed is "X", and a case in which the reduction effect thereof is "Y". The AEC parameter setting unit 102 obtains, from the image processing parameter, ON/OFF of the scattered ray reduction processing, ON/OFF of the noise reduction processing, and the noise reduction effect of the noise reduction processing, obtains the target dose for AEC from the table, and sets it for the AEC. The relationship between the noise reduction effect and the target dose will be described in the fourth embodiment.

Further, the target dose corresponding to the reduction effect of the scattered ray reduction processing may be set. The low reduction effect in the scattered ray reduction processing is equivalent to the effect obtained by imaging using a grid having a high transmission rate (a low grid ratio). Therefore, using a table 5*d* shown in FIG. 5, the target dose in AEC may be changed in accordance with the reduction effect of the scattered ray reduction processing. For example, the target dose in AEC may be set to the target dose for a case in which the grid corresponding to the reduction effect of the scattered ray reduction processing is used. However, the present invention is not limited to the above-described examples, and the target dose may be prepared for each of the types (scattered ray estimation methods) of the scattered ray reduction processing. In an arrangement in which the sensitivity of a dose detection sensor 212 is switchable, the target dose may be prepared for each sensitivity. In the embodiment described above, the target dose is stored in the table, but the present invention is not limited to this. For example, a coefficient to be multiplied by the corrected target dose Th1 obtained in the first embodiment may be stored in each of the tables 5*b* to 5*d* shown in FIG. 5.

Third Embodiment

In the first embodiment, a configuration has been described in which the scattered ray reduction processing and use of the grid are exclusive, and if the scattered ray reduction processing is ON, the target dose assuming use of the grid is corrected. In the third embodiment, setting of a target dose in accordance with ON/OFF of grid pattern reduction processing assuming use of a grid will be described. In the third embodiment, by using the grid pattern reduction processing and the scattered ray reduction processing together, a case may occur in which the scattered ray reduction processing is executed while using the grid. The functional arrangement and hardware arrangement of a radiation imaging system according to the third embodiment are similar to those in the first embodiment (FIGS. 1 and 2). An operation of the radiation imaging system according to the third embodiment will be described below using the flowchart of FIG. 3.

In the third embodiment, a target dose correction method in step S303 is different from that in the first embodiment. An AEC parameter setting unit 102 obtains an AEC-related parameter and an image processing parameter (step S302). Assume that the image processing parameter indicates that the scattered ray reduction processing is ON and the grid pattern reduction processing is also ON. This is a case in which the grid is used together with the scattered ray reduction processing. In this case, from the grid information associated with the grid pattern reduction processing as the image processing parameter, a transmission rate T1 of the grid currently in use is calculated by equation (2), and a target dose Th2 corrected using the transmission rate T1 is obtained. Note that in equation (2), as in the first embodiment, Th0 is the target dose obtained in step S302, and T0 is the transmission rate of the grid assumed by the target dose:

$$Th2=(Th0/T0) \times T1 \qquad (2)$$

By executing correction as described above, even in a case in which both the grid pattern reduction processing and the scattered ray reduction processing are ON and a grid different from the grid which the target dose obtained in step S302 corresponds to is used, the target dose can be correctly maintained. That is, even if the grid and the scattered ray reduction processing are used at the same time, it is possible to execute radiation imaging with the irradiation amount equal to the irradiation amount intended by the target dose obtained in step S302. This can prevent a deterioration in image quality.

Note that in the above description, the case in which the grid pattern reduction processing and the scattered ray reduction processing are used together has been described. However, even in a case in which only the grid pattern reduction processing is applied, by using the target dose correction expressed by equation (2) described above, it is possible to appropriately maintain the irradiation amount of radiation during radiation imaging.

Fourth Embodiment

In the fourth embodiment, still another embodiment of the target dose correction method executed in step S303 will be described. One of post-processing operations of a radiation image is noise reduction processing. The noise reduction processing is processing of removing noise components based on the relationship with peripheral pixels. This can convert even a noisy image into an image that improves the diagnostic performance of a doctor. Therefore, by using the noise reduction processing, imaging with a low dose becomes possible. The target dose is changed in accordance with ON/OFF of the scattered ray reduction processing in the first embodiment, but in the fourth embodiment, the target dose is changed in accordance with ON/OFF of the noise reduction processing and the noise reduction amount thereof to implement radiation imaging with an appropriate irradiation dose. That is, in the fourth embodiment, an image processing parameter includes a noise reduction parameter related to the noise reduction processing. An AEC parameter setting unit 102 sets a target dose based on the noise reduction parameter, thereby implementing imaging with an appropriate radiation dose.

The AEC parameter setting unit 102 obtains an AEC-related parameter and an image processing parameter. The image processing parameter includes a parameter indicating the reduction effect of the noise reduction processing. For example, in a case of a still image, the noise reduction processing is filtering processing using a filter or a bilateral filter, and in a case of a moving image, the noise reduction processing is filtering processing using a recursive filter. Even if a noisy radiation image is obtained by imaging with a suppressed irradiation dose, an image quality suitable for diagnosis can be obtained by using the noise reduction processing. However, if the target dose in AEC remains the same, the irradiation dose is not changed. That is, even though the noise reduction effect is increased, the irradiation dose during radiation imaging is not decreased. Therefore, it is preferable to change the target dose in accordance with the noise reduction effect.

In the second embodiment, this is implemented by employing the table 5c shown in FIG. 5, but in the fourth embodiment, a configuration will be described in which the target dose obtained in step S302 is corrected. According to the target dose correction processing in the fourth embodiment, the target dose is decreased as the noise reduction effect is increased. With this, it is possible to obtain the appropriate image quality while suppressing the irradiation dose. Letting D be the dose entering a radiation sensor 202, random noise $\sigma_q$ caused by it is expressed as equation (3) using a conversion coefficient $K_q$:

$$\sigma_q = K_q \times \sqrt{(D)} \quad (3)$$

In addition to the noise caused by the radiation as expressed by equation (3), electrical noise is also added onto the radiation image. However, assuming that the amount of electrical noise is negligible here, if the noise is increased to 1/a times by the noise reduction, the target dose can be corrected to $1/a^2$ according to equation (3). That is, if the scattered ray reduction processing and the noise reduction processing are used together, a corrected target dose Th1 is expressed as following equation (4). Note that T0 is the radiation transmission rate of the grid calculated from the grid information, and Th0 is the target dose in a case of using the grid:

$$Th1 = (Th0/T0)/a^2 \quad (4)$$

Fifth Embodiment

In the first embodiment described above, a configuration has been described in which the AEC parameter setting unit 102 automatically corrects the target dose in AEC based on the image processing parameter in step S303. In the fifth embodiment, a configuration will be described in which a user is inquired whether to execute correction in step S303. That is, when setting a target dose different from the target dose for a case of using a grid, an AEC parameter setting unit 102 displays a message indicating that the target dose is to be changed, and checks a user instruction indicating permission/non-permission of the change.

The AEC parameter setting unit 102 obtains an AEC-related parameter (AEC parameter) and an image processing parameter. If it is determined from the obtained image processing parameter that the target dose designated by the AEC parameter needs to be changed, the AEC parameter setting unit 102 causes a display unit 209 to display a confirmation message via an output unit 108. The confirmation message represents contents that prompt the user to confirm automatic correction of the target dose. If the correction is permitted by the user, the AEC parameter setting unit 102 executes the correction of the target dose. On the other hand, if the correction is not permitted, the AEC parameter setting unit 102 does not correct the target dose, and uses the target dose obtained from the AEC parameter intact even if scattered ray reduction processing is ON.

As has been described above, according to the fifth embodiment, the user can select whether to execute automatic correction of the target dose.

Note that in each of the above-described embodiments, imaging of a still image has been described, but the present invention is not limited to this. For example, the above-described target dose setting method may be applied to a combination of a dose control mechanism and image processing used in a fluoroscope apparatus or the like. For example, by correcting the target dose of the fluoroscope in the manner similar to that described above, a similar effect can be obtained. Before starting radiation imaging, a grid may be detected, and it may be checked whether the setting of the target dose in AEC matches the presence/absence of the grid. If they do not match, a warning about the mismatch may be output. Further, the target dose may be adjustable by multiplying the target dose obtained in each embodiment by a coefficient $\alpha$ ($\alpha > 0$). In this case, if the user can set the value of α, the target dose can be adjusted in accordance with user preference. For example, if this is applied to the configuration according to the first embodiment, the corrected target dose Th1 obtained by equation (1) is multiplied by α set by the user, and α×Th1 is set as the target dose in AEC.

According to the present invention, it is possible to execute radiation imaging with an appropriate radiation dose by controlling setting of a target dose in automatic exposure control.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A control apparatus that controls, using automatic exposure control of controlling a radiation generation apparatus by comparing a radiation dose relating to radiation from the radiation generation apparatus with a target dose, radiation imaging using radiation from the radiation generation apparatus, comprising:
a setting unit configured to set a target dose determined based on an image processing parameter selected according to an instruction by an operator from among a plurality of image processing parameters relating to a radiation image obtained by the radiation imaging, as the target dose used by the automatic exposure control,
wherein if the selected image processing parameter indicates that scattered ray reduction processing is to be executed, the setting unit sets a first target dose as the target dose used by the automatic exposure control, and if the selected image processing parameter indicates that scattered ray reduction processing is not to be executed, the setting unit sets a second target dose different from the first target dose as the target dosed used by the automatic exposure control.

2. The control apparatus according to claim 1, wherein the first target dose is higher than the second target dose.

3. The control apparatus according to claim 1, wherein a ratio of the first target dose and the second target dose is equal to a transmission rate of a grid to which the second target dose is applied.

4. The control apparatus according to claim 1, wherein if the selected image processing parameter indicates that scattered ray reduction processing is to be executed, the setting unit sets a target dose obtained by correcting a target dose applied when using a grid based on a transmission rate of the grid, as the target dose used by the automatic exposure control.

5. The control apparatus according to claim 1, wherein the control apparatus holds a table storing a plurality of target doses corresponding to the plurality of image processing parameters, and
the setting unit sets, as the target dose used by the automatic exposure control, the target dose related to the selected image processing parameter from the plurality of target doses stored in the table.

6. The control apparatus according to claim 5, wherein the plurality of target doses include a target dose for a case of executing scattered ray reduction processing and a target dose for a case of executing no scattered ray reduction processing.

7. The control apparatus according to claim 5, wherein the plurality of target doses include target doses each corresponding to a grid specification, and
if the selected image processing parameter indicates that no scattered ray reduction processing is to be executed, the setting unit sets a target dose corresponding to the grid specification indicated by grid information as the target dose used by the automatic exposure control.

8. The control apparatus according to claim 1, wherein the setting unit further comprises a check unit configured to, when setting a target dose different from a target dose for a case of using a grid, display a message indicating that the target dose is to be changed, and check a user instruction indicating permission/non-permission of the change.

9. A radiation imaging system comprising:
a control apparatus according to claim 1;
the radiation generation apparatus; and
a detection unit configured to detect a radiation dose from the radiation generation unit.

10. A control apparatus that controls, using automatic exposure control of controlling a radiation generation apparatus by comparing a radiation dose relating to radiation from the radiation generation apparatus with a target dose, radiation imaging using radiation from the radiation generation apparatus, comprising:
a setting unit configured to set a target dose determined based on an image processing parameter selected according to an instruction by an operator from among a plurality of image processing parameters relating to a radiation image obtained by the radiation imaging, as the target dose used by the automatic exposure control, wherein
the setting unit sets a target dose determined based on information regarding use/non-use of grids determined from the selected image processing parameter is set as the target dose used by the automatic exposure control.

11. A control apparatus that controls, using automatic exposure control of controlling a radiation generation apparatus by comparing a radiation dose relating to radiation from the radiation generation apparatus with a target dose, radiation imaging using radiation from the radiation generation apparatus, comprising:
a setting unit configured to set a target dose determined based on an image processing parameter selected according to an instruction by an operator from among a plurality of image processing parameters relating to a radiation image obtained by the radiation imaging, as the target dose used by the automatic exposure control, wherein
in a case where the selected image processing parameter includes a parameter for grid pattern reduction processing or a noise reduction parameter, the target dose is determined based on a transmission rate of a grid corresponding to the grid pattern reduction processing or the noise reduction parameter.

12. A control method for controlling, using automatic exposure control of controlling a radiation generation apparatus by comparing a radiation dose relating to radiation from the radiation generation apparatus with a target dose, radiation imaging using radiation from the radiation generation apparatus, the method comprising:
setting a target dose determined based on an image processing parameter selected according to an instruction by an operator from among a plurality of image processing parameters relating to a radiation image obtained by the radiation imaging, as the target dose used by the automatic exposure control, wherein if the selected image processing parameter indicates that scattered ray reduction processing is to be executed, a first target dose is set as the target dose used by the automatic exposure control, and if the selected image processing parameter indicates that scattered ray reduction processing is not to be executed, a second target dose different from the first target dose is set as the target dosed by the automatic exposure control.

13. A non-transitory computer-readable storage medium storing a program for causing a computer to execute a control method according to claim 12.

14. A control apparatus that controls, using automatic exposure control of controlling a radiation generation apparatus by comparing a radiation dose relating to radiation from the radiation generation apparatus with a target dose, radiation imaging using radiation from the radiation generation apparatus, comprising:
a setting unit configured to set a target dose determined based on information relating to a grid selected in accordance with an instruction by an operator from among a plurality of pieces of information relating to a plurality of grids, as the target dose used by the automatic exposure control.

15. The control apparatus according to claim 14, wherein the setting unit sets a first target dose as the target dose used by the automatic exposure control when the selected information relating to a grid represents use of a grid, and sets a second target dose different from the first target dose as the target dose used by the automatic exposure control when the selected information relating to a grid represents non-use of a grid.

16. A control method for controlling, using automatic exposure control of controlling a radiation generation apparatus by comparing a radiation dose relating to radiation from the radiation generation apparatus with a target dose, radiation imaging using radiation from the radiation generation apparatus, the method comprising:
setting a target dose determined based on information relating to a grid selected in accordance with an instruction by an operator from among a plurality of pieces of information relating to a plurality of grids, as the target dose used by the automatic exposure control.

17. A non-transitory computer-readable storage medium storing a program for causing a computer to execute a control method according to claim 16.

* * * * *